(12) United States Patent
Johal

(10) Patent No.: US 7,846,463 B2
(45) Date of Patent: Dec. 7, 2010

(54) PEST CONTROL COMPOSITION AND METHOD

(75) Inventor: Sarjit Johal, Iowa City, IA (US)

(73) Assignee: Grain Processing Corporation, Muscatine, IA (US)

(*) Notice: Subject to any disclaimer, the term of this patent is extended or adjusted under 35 U.S.C. 154(b) by 571 days.

(21) Appl. No.: 11/382,878

(22) Filed: May 11, 2006

(65) Prior Publication Data

US 2006/0257443 A1   Nov. 16, 2006

Related U.S. Application Data

(60) Provisional application No. 60/679,908, filed on May 11, 2005.

(51) Int. Cl.
 *A01N 25/00* (2006.01)
 *A01N 25/12* (2006.01)
 *A01N 65/44* (2006.01)

(52) U.S. Cl. .................. 424/405; 424/408; 424/731

(58) Field of Classification Search ............ 424/489, 424/405, 408, 731; 514/943
See application file for complete search history.

(56) References Cited

U.S. PATENT DOCUMENTS

| | | | |
|---|---|---|---|
| 4,238,484 A | 12/1980 | Stein et al. | |
| 4,804,142 A * | 2/1989 | Riley | 239/56 |
| 4,911,952 A | 3/1990 | Doane et al. | |
| 4,983,390 A | 1/1991 | Levy | |
| RE33,670 E | 8/1991 | Maglio | |
| 5,063,232 A | 11/1991 | Leyendecker et al. | |
| 5,290,557 A | 3/1994 | Mason et al. | |
| 5,437,870 A | 8/1995 | Puritch et al. | |
| 5,571,522 A * | 11/1996 | Munson et al. | 424/410 |
| 5,607,684 A | 3/1997 | Lew et al. | |
| 5,609,880 A | 3/1997 | Munson et al. | |
| 5,639,319 A | 6/1997 | Daly | |
| 5,658,954 A | 8/1997 | Targosz | |
| 5,690,951 A | 11/1997 | Lew et al. | |
| 5,885,600 A * | 3/1999 | Blum et al. | 424/405 |
| 5,939,061 A | 8/1999 | Vail et al. | |
| 5,968,540 A | 10/1999 | Brenner et al. | |
| 5,997,445 A | 12/1999 | Maresh et al. | |
| 6,159,489 A | 12/2000 | Sakurada et al. | |
| 6,174,538 B1 | 1/2001 | Branly et al. | |
| 6,187,326 B1 | 2/2001 | Yamashita | |
| 6,316,447 B1 | 11/2001 | Nakamura et al. | |
| 6,335,027 B1 | 1/2002 | Levy | |
| 6,340,656 B1 | 1/2002 | Takayanagi et al. | |
| 6,368,588 B1 | 4/2002 | Faehl et al. | |
| 6,384,082 B1 | 5/2002 | Wirth et al. | |
| 6,391,328 B1 | 5/2002 | Levy | |
| 6,524,600 B2 | 2/2003 | Yamashita | |
| 6,602,804 B2 | 8/2003 | Allen et al. | |
| 2001/0000325 A1 | 4/2001 | Yamashita | |
| 2003/0020043 A1 | 1/2003 | Barresi et al. | |
| 2003/0162664 A1 | 8/2003 | Walker | |
| 2004/0086541 A1 | 5/2004 | Barresi et al. | |
| 2004/0223998 A1 * | 11/2004 | Iyer et al. | 424/405 |

FOREIGN PATENT DOCUMENTS

| | | |
|---|---|---|
| EP | 0115664 | 8/1984 |
| EP | 0145846 A2 | 6/1985 |
| EP | 0340948 | 11/1989 |
| EP | 0384251 | 8/1990 |
| EP | 0469690 | 2/1992 |
| EP | 0598746 | 9/1996 |
| EP | 0725562 | 8/1998 |
| EP | 1052899 | 4/2002 |
| EP | 1107666 | 11/2002 |
| EP | 1306008 A1 | 2/2003 |
| JP | 61106505 | 5/1986 |
| JP | 2002087914 | 3/2002 |
| SU | 67694 | 12/1946 |
| WO | WO 2004034791 A1 * | 4/2004 |

OTHER PUBLICATIONS

Ban. The Efficiency of Volatile Ingredients in Neem Oil Against Callosobrushus Chinensis (Coleoprera: Bruchidae), (Abstract) Techincal Bulletin of Faculty of Agriculture, Kagawa University [online], [retrieved on Sep. 18, 2009]. Retrieved from the Internet <URL: http://sciencelinks.jp/j-east/article/200014/000020001400A0428646.php.*
Shaw, Roll-On Insect Repellent, Mar. 1971, Canadan Patent, CA 865069 A, Derwent Abstract, pp. 1-2.*
Kampen, Willem H. et al., Abstract: "Value-added Products from Stillage of Ethanol-from-molasses and Corn-to-ethanol plants", Publication of Technical Papers and Proceedings of the Annual Meeting of Sugar Industry Technologists (1999), Baton Rouge, LA.
Kepner, R.L. et al., Abstract: "Development of a toxic bait for control of mole crickets", Journal of Economic Entomology, Gainesville, FL 1987.
McDaniel, E.I., Abstract: "The Control of certain household pets with poison bran bait", Mich. Agr. Expt. Sta., Quart. Bull. 1934.
CN Office Action May 8, 2008, CN App. 2546209.

* cited by examiner (Continued)

Primary Examiner—Johann R Richter
Assistant Examiner—Andriae M Holt
(74) Attorney, Agent, or Firm—Fitch Even Tabin & Flannery

(57) ABSTRACT

Disclosed is a pest control composition that includes a pest control agent, such as citronella oil, and a carrier, the carrier comprising a cellulosic fibrous material and a mineral sorbent material. In preferred embodiments to the invention, the composition is in the form of discrete plural compacted particles. Surprisingly, a pest control composition prepared in accordance with the preferred embodiments of the invention is substantially dry to the touch and permits sustained release of the pest control agent. Methods for preparing a pest control agents and method for pest control also are disclosed.

8 Claims, No Drawings

PEST CONTROL COMPOSITION AND METHOD

BEST CONTROL COMPOSITION AND METHOD

This application claims priority to prior provisional U.S. patent application Ser. No. 60/679,908, filed May 11, 2005. The contents of the prior application are hereby incorporated by reference in their entireties.

FIELD OF THE INVENTION

This invention is in the filed of pest control compositions and methods.

BACKGROUND OF THE INVENTION

Pest control agents are materials that limit the growth or spread of a living thing, such as by repelling, killing, preventing, or otherwise. Numerous pest control agents are known in the art, and many methods for introducing such a pest control agent into an environment also are known. For instance, the prior art has taught various repellents for pests such as rabbit, deer, dog, cat, squirrel, bird, mole, and mosquito. Repellents can broadly be defined as compositions that prevent, deter, or minimize pests from entering or remaining in target pest area. Repellents that are non-lethal at normally applied doses are available; in some cases, the same chemical used at low levels exhibits non-lethal repellency whereas use at higher levels is lethal. The prior art has also taught numerous pesticidal control agents and other types of control agents.

Many control agents take the form of oils, such as fragrant botanical oils. As one example, citronella oils are well known for efficacy in controlling mosquitoes by repelling mosquitoes from an area in which citronella oils are present. Botanical oils are advantageous for numerous reasons. Such oils are stable, are often strongly recognized by the target pest, and can be highly selective to the targeted pest. In some cases, even a few molecules of an appropriate agent can exhibit a strong response in the target pest while otherwise not affecting the local ecosystem.

Many commercially available botanical oils are formulated for delivery as aqueous sprays, which typically require employment of a hose-end sprayer for application. However, such liquid delivery systems are not desirable, because they are inefficient at controlling release of the volatile substances. Many botanical oils are expensive and available in limited quantities, and there is competition for such materials by for example, the food flavorings and fragrances industries. Accordingly, it is desirable to avoid waste and over-application of such oils.

Oils are generally liquid at the intended temperature of application. Although liquid oils are useful in many applications, in some case it is desirable to provide solid pest control formulations. Solid pest control products have a number of advantages in targeting an area for pest control. For instance, solid compositions often are more easily handled and applied then liquid compositions. For this reason, the prior art has provided numerous forms of solid pesticides and repellents, a familiar example of which is the citronella candle. In such cases, the majority of the solid pest control composition is composed of a carrier or sorbent material, the balance comprising the active ingredient. Generally, the active ingredient comprises a small percentage (less then about 10%) of the weight of the composition.

Certain plant-based sorbent materials have been proposed as carriers for use with pesticides and other control agents. For instance, materials such as corn cob, peanut hulls, starches, and the like have been proposed as carriers or pesticides for providing a solid control agent composition. Although such materials are useful and enjoy a number of advantages, in some respects the use of such materials suffers from certain drawbacks. For instance, when used with a lipophilic or oleolgenous control agent, the resulting composition can be oily to the touch. Additionally, when used with a fragrant repellent oil, such as citronella oil, the oil generally is released from the composition more rapidly than is often desired, thus necessitating more frequent application of the pest control composition. In many cases, it is desired to introduce the control agent into an environment in a sustained-release manner, by which is contemplated that at least some of the control agent is bound up with another material or otherwise is not immediately able to function in the environment for its intended purpose.

In some cases, particularly when the control agent comprises a botanical oil, it is desirable to provide a sorbent that allows sustained release of at least some of the control agent into an environment. U.S. patent application Ser. No. 10/172,588 and U.S. patent application Ser. No. 10/696,374, both assigned to Grain Processing Corporation of Muscatine, Iowa, contain excellent teachings as to pest control compositions, the compositions based, inter alia on corn germ or seed meal. As taught therein, a pest control composition, such a larvicide or the like, may be sorbed within a carrier. The carrier may comprise for instance, a spent corn germ sorbent. The resulting composition may be pelleted to form discrete plural particles. It has been observed that, while the foregoing compositions are suitable for use for a wide range of control agents (including botanical oils), for some oils the particles prepared in accordance with these teachings sometimes can feel oily to the touch.

The present invention seeks to provide a pest control composition that, in preferred embodiments, is in the form of discrete plural particles of a control agent sorbed within a carrier. In preferred embodiments, the invention seeks to provide a composition in the form of solid particles that are not substantially "oily" to the touch and that enable sustained-release of the control agent contained therewithin.

THE INVENTION

It is now been found that a control agent composition may be prepared using a control agent and a carrier. In accordance with the invention, the carrier comprises a cellulosic fibrous sorbent material and mineral sorbent material. Preferably, the composition takes the form of discrete plural compacted particles. In highly preferred embodiments, the particles take the form of crumbled pelleted particles produced in a commercial-scale pellet mill. Surprisingly, it has been found that the use of a cellulosic fibrous material in conjunction with a mineral sorbent material can provide sustained-release properties that are unexpectedly superior to the properties expected of a composition prepared using either component of the carrier alone. Additionally, the discrete plural particles prepared in accordance with the preferred embodiments of the present invention are not oily to the touch. In highly preferred embodiments, the mineral sorbent is a bentonite clay, the cellulosic fibrous sorbent material is a corn cob residue, and the control agent is a citronella oil.

The invention is also directed towards a method for pest control, the method comprising distributing to a target area an amount of pest control composition as described hereinabove affected to control at least one pest. The discrete plural particles prepared in accordance with the present teachings may be distributed onto a target pest control area, such as a patio, outdoor area, and so forth. Also encompassed by the present invention is a method for preparing a pest control composition, the method comprising providing the component ingredients of the composition and, under appropriate conditions as taught herein, forming discrete plural compacted particles therefrom.

Other features and embodiments of the invention are described hereinbelow and are encompassed by the pending claims.

DETAILED DESCRIPTION OF THE PREFERRED EMBODIMENTS

The invention contemplates the use of a sorbent carrier. Generally, the term "sorbent" contemplates a material that absorbs and/or adsorbs another material. Absorption is a term used in the art to refer to the penetration of one substance into the inner structure of another substance, whereas the term adsorption refer to adherence of atoms, ions, or molecules onto the surface of another material. It is believed that one or both phenomena occur in accordance with the various embodiments of the invention, but it is contemplated that the material may serve as a sorbent even if only one of the two phenomena is present. By "sorbed within" is herein contemplated the sorption of a material in or on the sorbent.

Generally, the invention contemplates a sorbent carrier that includes a cellulosic fibrous sorbent material and a mineral sorbent material. Although, as stated hereinabove, the preferred cellulosic fibrous material comprises ground corn cob, any suitable cellulosic material may be used in conjunction with the invention. For instance, the cellulosic material may comprise a purified modified cellulose fibrous material, wood pulp, saw dust, cork, bagasse, seed, seed hulls, such as rice, rice hulls, wheat, wheat hulls, barley, barley hulls, and the like. Many of these materials are agricultural by-products; generally, it is contemplated that other suitable agricultural by-product may be employed in conjunction with the invention.

In some embodiments, the cellulosic fibrous sorbent used in conjunction with the invention includes a grain germ, such as virgin grain germ or spent grain germ. As is known in the art, spent germ comprises a germ from which oil has been expelled, for instance, by pressing or extraction with an extracting liquid such as hexane or water. Virgin germ (i.e., germ from which oil has not been extracted) also or alternatively may also be used. Germ obtained from any suitable grain may be employed in conjunction with the invention, suitable grains including, for instance, corn, wheat, soy, sorghum, barley, and the like.

Spent grain germ is able to sorb both hydrophilic and lipophilic control agents. When used in conjunction with the invention, the spent germ preferably is washed to render it substantially free of odor components; although in other embodiments, unwashed germ may be used.

Alternatively, or in addition thereto, the sorbent used in conjunction with the invention may be a seed meal. Examples of such meals include linseed meal, soybean meal, sunflower meal, cottonseed meal, rapeseed meal, peanut meal, safflower seed meal, and combinations thereof. By "seed" is meant to include that part of a plant which is capable of forming a new plant upon germination, e.g., whole grains of wheat, including the fruit or fruit-like structure housing the seed. The seed meal comprises a spent oil bearing seed residue, which is a seed residue from which oil has been expelled, such as by solvent extraction or expeller extraction. The extracted residue then is ground, by which is contemplated the reduction of the residue to smaller particles, preferably to a semi-course to fine powder. It is contemplated that some seeds will include a hull that may (but need not) be removed prior to expelling oil and grinding. Thus, the meal may comprise a dehulled meal. The seed meal in some embodiments is washed to substantially remove odor components therefrom.

Otherwise, any suitable cellulosic fibrous sorbent material may be used in conjunction with the invention. The cellulosic fibrous component of the carrier may comprise mixtures of two or more of the foregoing, such as corn germ and ground corn cob. In such cases, the plural cellulosic fibrous materials may be used in any amounts relative to one another.

Another component of the carrier used in conjunction with the invention is a mineral sorbent. The mineral sorbent is preferably bentonite clay, but any suitable mineral sorbent material may be used in conjunction with the invention. By "mineral sorbent" is contemplated any mineral or mineraloid substance that is capable of functioning as a sorbent carrier in conjunction with the control agent of the composition. For instance, mineral silicates, carbonates, sulfates, halides, oxides, and so forth are contemplated to be suitable for use in conjunction with the invention. Clays, or hydrous silicates, are deemed particularly suitable for use in conjunction with the invention, with the most highly preferred clay being bentonite. The mineral sorbent portion of the carrier may comprise two or more mineral sorbents, which may be present in any amounts relative to one another.

The cellulosic fibrous sorbent and mineral sorbent may be present in any suitable amount with respect to one another. For instance, with respect to the total weight of the mineral sorbent and cellulosic fibrous sorbent components present in the composition, the cellulosic fibrous sorbent may be present in an amount of 5%, 10%, 15%, 20%, 25%, 30%, 35%, 40%, 45%, 50%, 55%, 60%, 65%, 70%, 75%, 80%, 85%, 90% or 95% by weight.

Although it is not intended to limit the invention to a particular theory of operation, it is believed that the present invention allows for a surprisingly sustained-release property relative to use of either a cellulosic fibrous sorbent or a mineral sorbent alone. It is believed that the cellulosic fibrous sorbent and mineral sorbent have different pore sizes, and the use of these sorbents together provides enhanced retention of the control agent, particularly when the control agent is a fragrant oil. Further, it is believed that the combination of two different types of absorbent plant fiber provides a composite having varying voids and porosities, such that each of the different plant fiber materials contributes a different structure. When the structures are combined together, a sustained release composite that allows volatilization of absorbed/entrapped oil over an extended period of time is produced. In any case, as detailed in the examples hereinbelow, the invention permits excellent sustained-release properties.

The pest control composition of the invention incorporates a pest control agent, by which is contemplated any material, generally a liquid at room temperature, that is capable of killing, repelling, sterilizing, destroying eggs of, preventing birth of, or otherwise controlling a targeted pest. The pest can be any organism whose presence in the environment is undesired. The pest may be present in the environment, or may not be present in the environment (in other words, it is contemplated that the environment may be treated prophylactically). Any organism found in the Animalia, Protista, Fungi (in particular non-mold fingi), Plantae, or Monera kingdoms may be deemed a pest in particular circumstances, and the control agent may be any agent that limits the growth of such pest in the environment.

With respect to animals, the pest may be mammal, for instance, a rodent such as a mouse or rat, or a non-mammal, such as a fish, bird or other animal. The invention is believed to be particularly applicable to the control of animals in the phylum Arthropoda, including especially the classes Insecta (representing insects, millipedes, and centipedes), and Cheliceramorpha, especially arachnids. The control agent in preferred embodiments may be a rodenticide, a herbicide, an insecticide, a fungicide, or a bactericide. Specific embodiments of the invention employ, for instance, a larvicide, a pupicide, an ovicide, a hormone, a growth regulator (e.g. an insect growth regulator), a biological control agent, a microbial control agent, a toxicant, a fumigant, a pheromone, a repellent, a chemosterilant, a miticide, an acarcide, a molluscicide, an avicide, a predicide, an algaecide, a nematicide, an amoebicide, a nymphicide, and the like. In preferred embodiments, the control agent is selected from among an animal control agent (which may be a control agent for any species in the kingdom Animalia), a plant control agent (any species which may be a control agent for any species in the kingdom Plantae), a non-mold fungal control agent (which may be a control agent for any species in the kingdom Fungi, excepting the molds), a protest control agent (which may be a control agent for any species in the kingdom Protista) or a mineral control agent (which may be a bacterial species or any other species in the Monera kingdom). In some embodiments, the control agent may be a virus control agent. Two or more agents can be combined to increase efficacy or to achieve multifunctional performance in the same composition.

Specific examples of suitable control agents include insecticides such as temephos, chlorpyfifos, methyl isocyanate, methoprene, propaphos, DURSBAN dimilin, malathien, carbaryl, and diazinon; herbicides such as 2,4-D and 2,4-D ester, ammonium sulfamate, BROMACIL, copper salts, molinate, propanil, pyrazolate, metolachlor, and the like. Other control agents include bioactives such as *Bacillus thuringiensis* and *Bacillus sphaericus*; fungicides, such as fenoxanil, iprobenfos, menopril, tricyclozole, and valdamycin, and the like. U.S. Pat. Nos. 4,911,952; 4,983,390; 5,997,445; 6,159,489; 6,316,447; 6,335,027; and 6,340,656, all disclose numerous control agents, any or all which in certain embodiments may be deemed suitable for use in conjunction with the invention.

In highly preferred embodiments of the invention, the agent is a fragrant volatile or non-volatile botanic oil that is effective in repelling a targeted pest. Suitable oils include garlic oil, castor oil, citronella oil, lemon grass oil, wheat oil, oil of anise, coriander oil, rosemary, capsicum (pepper) oil, neem oil, and so forth. Mixtures of the foregoing oils may be used, and the oils generally may be volatile, non-volatile, or a mixture of oils, one or more of which is volatile and one or more of which is not volatile. Different oils are preferred for different targeted pests. When the pest control composition is to be used as a mosquito control composition, the preferred oil is citronella oil. When the pest control composition is a mole repellent composition, the control agent is preferably castor oil. These oils may be augmented with other oils, such as garlic oil. It is contemplated that the oils will be released upon volatilization of the oil. If desired, other oils, hydrocarbons, or other ingredients that modify the viscosity and volatilization attributes of the active agent may be included.

The control agent may be present in any amount suitable for use in the pest composition when a pesticidal composition is employed. Preferably, the control agent is present in the amount ranging from 0.001% to 50% by weight of the composition, more preferably, from 0.001% to 10% by weight of the composition, and even more preferably, 0.005% to 5% by weight of the composition. In some embodiments, the control agent is present in the amount of 0.05% to 1%, or, within this range, from 0.05% to 0.5% by weight. When a repellent oil is employed, the oil or mixture of oils may be present in the foregoing amounts, but more preferably is present in amounts ranging from 5%-15% by weight of the composition. More generally, any amount of control agent suitable for use with the intended purposes of the composition may be employed.

The pest control composition may be formulated using exclusively a carrier and a control agent as described hereinabove. Optionally, the composition may include any other additives, which may be present in any amounts suitable for their intended purposes or omitted altogether. Examples of such additives include surfactants, spreading agents, adjuvants, other carriers, binders, deflocculating agents, dispersing agents, synergists, penetrants, suspending agents, baits (not used in repellent compositions), phagostimulants, sticking agents, stabilizers, coupling agents, foaming or antifoaming agents, diluents, waxes, oils, superabsorbents, and more generally, any other additives. Such additives may be present in amounts suitable for their intended purpose. For instance, Yucca and Mohave extracts have been observed to be suitable for use as surfactants in conjunction with the invention. These surfactants are believed to aid in the release of oils from the composition, particularly when the composition takes the form of a pest control agent. In some embodiments, the composition includes a drying agent in an amount effective to provide a composite that is dry to the touch.

The composition that includes the sorbent and sorbed material (including any additives) may be provided in any suitable form. Most preferably, the composition is provided in the form of discrete plural compacted particles of a substantially uniform and homogenous admixture of the sorbent and the sorbed materials. The composition of the invention preferably takes the form of discrete plural compacted particles. It is contemplated that a coating may be used in conjunction with the invention, such that the particles comprise wholly or partially coated particles. However, in preferred embodiments the invention, the particles are not coated subsequent to formation of the particles, i.e., the invention takes the form of uncoated particles. Although coatings may provide satisfactory results, a composition prepared without a coating generally will be less expensive to prepare then an otherwise similar coated composition.

The particles may be prepared in any suitable manner. In a highly preferred embodiment of the invention, the particles are prepared by pelletizing at least the carrier ingredients of the pest control composition in a pellet mill, with or without added moisture as may be deemed appropriate. The composition may be prepared by sorbing the control agent into pellets thus formed, or alternatively may be prepared by pelletizing a mixture of the control agent and the sorbent. In either case, the pellets exiting the pellet mill may be ground or crumbled to thereby reduce the pellets to a desired particle size. As set forth in more detail hereinbelow, one or more binders may be employed.

The mixture may be pelletized under any suitable conditions. Typically, the ingredients are pre-ground and are introduced into the pellet mill, with or without added moisture. The typical moisture content in the pellet mill ranges from 2-30%, more preferably 5-15% by total weight of the blend. The blend is pelleted through a die such as a $\frac{3}{32}$ in.×2 in. die at any suitable temperature. Although lower temperatures generally are preferred, the temperature of the material in the pellet mill preferably ranges from 150° F. to 220° F., more preferably from 180° F. to 200° F. The final moisture of the pellets preferably is in the range from 4-20%, more preferably from 7-12% by total weight. If a drying agent is employed, such agent may be added at any time, preferably after the sorbents and active agent have been blended.

After pelleting, the pellets may be cooled and crumbled through dry rollers to reduce the size of the granules (it is also possible to cut the pellets from the die). The final granule size may vary depending on the application. For an application such as mosquito control, the granule size preferably should be between 4 and 30 mesh (U.S. standard test sieve. ASTM E-11 specification) and more preferably should be between 6 and 20 mesh. Fines generated during the pelletizing process may be removed by screening, preferable on a 10-mesh screen to a level of less than 20% by weight and ideally less than 5%. Such fines may be recycled.

In the pelletizing operation, use of a lubricity agent such as corn oil may be necessary or helpful. Other lubricants such as added corn oil or oils from soy, peanut, sunflower, rapeseed, canola, coconut, or cotton, or animal fats such as tallow, yellow grease, or white grease, may be used. Other lubricants include lecithin, waxes, fish oils, castor oil, long-chain alkyl sulphonates, alkyl polyglucosides, tall oil, stearates, and silicones.

The particles should be sufficiently cohesive for use for their intended purpose. Especially when the particle is used as a carrier for a control agent, the particle must have sufficient integrity to survive the production, transport, and application of the product. If the particle is too durable, however, it will not disintegrate easily, and may not be effective in releasing the control agent in the desired manner, for instance, when the particle is introduced into a water column. In embodiments of the invention where a delayed release of the control agent or other sorbed material is desired, the particles may be made more durable by incorporating additional binder or cohesiveness agent. The binder may comprise an extrudate of corn hulls and sodium hydroxide (as taught in U.S. Pat. No. 6,746, 698, issued Jun. 8, 2004 and assigned to Grain Processing Corporation of Muscatine, Iowa), lignin, lignosulfate, hemicelluloses, celluloses, water, starch hydrolyzates, hydrogenated starch hydrolyzates, fatty acids, and clay materials such as bentonite and zeolites. In such embodiments, the binder preferably is present in an amount of about 5% by weight of the particle. In some embodiments of the invention, the particles may include a polysaccharide cohesiveness agent to enhance the cohesiveness of the particles. The cohesiveness agent is believed to provide additional hydroxyl groups, which groups enhance the bonding between grain proteins within the sorbent particles. It is further believed that the additional hydroxyl groups so function by enhancing the hydrogen bonding of proteins to starch and to other proteins. When used, the polysaccharide cohesiveness agent may be present in any amount suitable to enhance the cohesiveness of the sorbent particles. Generally, the cohesiveness agent may be present in a dry basis amount ranging up to about 45% by weight of the sorbent particles, preferably, an amount ranging from about 3% to about 35% by weight, more preferably, an amount ranging from about 5% to about 25% by weight. When the binder is or includes virgin germ, some or all of this may come from starch naturally present in the virgin germ.

In accordance with these embodiments of the invention, any suitable polysaccharide may be used in conjunction with the invention, and thus, for example, the cohesiveness agent may comprise one or more polysaccharides such as dextrins, maltodextrins, starches, flours, cellulosics, hemicellulosics, and the like. Preferably, the cohesiveness agent comprises a starch, and most preferably, the cohesiveness agent comprises a corn starch.

When a polysaccharide cohesiveness agent is used, preferably a supplemental cohesiveness agent also is used. In accordance with the invention, the supplemental cohesiveness agent is an ionic species that is believed to enhance protein-protein and/or protein-starch interactions. Any suitable ionic salt may be used in conjunction with the invention. For example, in accordance with preferred embodiments of the invention, the supplemental cohesiveness agent is selected from among the alkali and alkaline-earth salts of common anions, such as the halide, nitrate, nitrite, carbonate, phosphate, sulfate, and bicarbonate salts, and the like. More preferably, the supplemental cohesiveness agent is selected from the group consisting of sodium chloride, calcium chloride, sodium carbonate, calcium carbonate, sodium bicarbonate and mixtures thereof. Even more preferably, the supplemental cohesiveness agent is selected from among sodium chloride, calcium carbonate, and mixtures thereof. Most preferably, the supplemental cohesiveness agent is sodium chloride. The supplemental cohesiveness agent may be present in any amount sufficient to assist the cohesiveness agent in enhancing the cohesion of the particles. When used, the supplemental cohesiveness agent preferably is present in an amount of at least about 0.05% by dry basis weight, of the composition exclusive of the polysaccharide cohesiveness agent. More preferably, the supplemental cohesiveness agent is present in an amount ranging from about 0.05% to about 10% by weight; more preferably, about 0.1% to about 8% by weight; and most preferably, about 1.5% to about 4% by weight. In a particularly preferred embodiment, the supplemental cohesiveness agent is present in an amount of about 2% by weight of the composition.

To prevent or inhibit spoilage, the sorbent composition may include a preservative. Preferably, the sorbent composition includes a mold inhibitor, which may be present in any amount sufficient to inhibit the molding of the sorbent composition. Any suitable mold inhibitor may be employed in conjunction with the invention. The mold inhibitor preferably is selected from among the propionate salts, and most preferably is selected from the group consisting of sodium propionate and calcium propionate. Other preservatives include sodium metabisulfite, citric acid, vitamin C, vitamin E, butylated hydroxytoluene (BHT) butylated hydroxyanisole (BHA), and sodium benzoate. When a mold inhibitor is employed, it preferably is present in an amount ranging from about 0.02% to about 3.5% by weight. The mold inhibitor may function to some extent as agent for controlling mold if the composition is introduced into an environment; however, at the levels used herein, the mold inhibitor is intended for the purpose of retarding mold of the composition itself.

The composition may be introduced into an environment via any suitable means. Where it is desired to disseminate the composition over a large area, the composition may be disseminated from an aircraft, such as plane, helicopter, blimp, balloon, or the like, or may be disseminated from a watercraft. Particularly when the control agent is a mosquito adulticide or larvicide, the environment may be a water-containing environment, by which is contemplated any environment containing standing or slowly moving water. For example, the water-containing environment may be a pond, lake, swamp, marsh, bog, area with collected rainwater, (such as a tire) and so forth. It is contemplated that in these or other embodiments of the invention the environment may be an indoor environment. In many cases, such as residential or light commercial use, the composition may be spread over a target area such as a deck, patio, or the like, or a quantity of the material may be placed in a single spot in the target environment. Lawn equipment, such as a rotary spreader, may be employed to disseminate the composition over a lawn or similar area.

The following examples are provided to illustrate the invention, but should not be construed as limiting the invention in scope.

EXAMPLE 1

A number of pest control compositions were prepared according to the following methodology: To a measured quantity of spent corn germ was added a botanical oil. The oil was added slowly, mixing with agitation. Ground corn cobs were added and blended with the fiber/oil mixture. The clay then was added and blended with the previously introduced mixture to form a blend.

Where indicated, the blend was introduced into a commercial pellet mill and pelletized. The resulting pellets were crumbled to form discrete plural particles.

EXAMPLE 2

A product of the invention prepared in accordance with the procedure set forth in Example 1 was compared to a similar product prepared from corn cobs and one prepared from spent corn germ. The products prepared solely from corn cobs and corn germ were not pelletized. The following observation were noted. For the "Residue on Paper" test, a quantity of the material under evaluation was placed onto a paper towel, and the existence and nature of any oil residue was observed.

| Absorption | | | |
|---|---|---|---|
| | Surface Attributes | | |
| | Uptake | Touch | Residue on Paper |
| Corn Cobs* | Excellent | Dry | Oily residue noted |
| Spent Corn Germ | Good | Oily/cake | Substantial |
| Composition 1** | Excellent | Dry/free flowing | None |
| Composition 1P⁺ | N/A | Dry/free Flowing | None |

*Corn cobs are particles/granules of ground corn cobs
**Composition 1 is the composition of Example 1, wherein the carrier included spent corn germ, ground corn cobs, and bentonite clay, not formed into pellets
⁺Composition 1P⁺ is the composition of Example 1, wherein the carrier included spent corn germ, ground corn cobs, and bentonite clay, formed into pellets Three of the foregoing compositions were evaluated for odor release. The compositions were applied to a surface and periodically evaluated for presence and strength of the fragrance of the botanical oils contained within the composition as determined by the inventor in an olfactory test. The following results were observed:

| Sustained Odor Release | | | | | | |
|---|---|---|---|---|---|---|
| | Days | | | | | |
| | 3 | 5 | 10 | 16 | 20 | 25 |
| Corn Cobs | 9 | 7 | 3 | 1 | 1 | 1 |
| Spent Corn Germ | 10 | 4 | 1 | 1 | 1 | 1 |
| Composition 1P⁺ | 7 | 6 | 7 | 5 | 4 | 4 |

As seen, the composition of the invention exhibited excellence sustained-release properties compared to compositions prepared using solely corn cobs or spent corn germ. Particularly after the tenth day, the composition of the invention exhibited a substantially stronger fragrance strength than that present in either the corn cob or spent corn germ composition.

EXAMPLE 3

A mosquito repellent was prepared using the hereinbefore discussed general methodology. The composition had the following ingredients:

| | |
|---|---|
| Castor Oil | 8.5% |
| Citronella Oil | 1.6% |
| Garlic Oil | 0.9% |
| Carrier: Corn cob (35% by total weight), spent corn germ (35%), and Bentonite Clay (19%) | 89.0% |
| | 100.0% |

EXAMPLE 4

A mole repellent was prepared using the hereinbefore discussed general methodology. The composition had the following ingredients:

| | |
|---|---|
| Castor Oil | 10.1% |
| Corn cob, spent corn germ, Bentonite Clay, Yucca Extract and Mohave Extract | 89.9% |
| | 100.0% |

EXAMPLE 5

A mole repellent is prepared using the hereinbefore discussed general methodology. The composition has the following ingredients:

| | |
|---|---|
| Castor Oil | 10% |
| Corn cob (35%), spent corn germ (35%), Bentonite Clay (20%) | 90% |
| | 100.0% |

EXAMPLE 6

A mosquito repellant product was manufactured using a production scale, fully integrated mixing-pelleting line.

First, a fragrant oil blend comprising castor oil, citronella oil and garlic oil was prepared and stored off-site until needed.

Commercially available corn cobs were added to a production scale mixing vessel. Under conditions of rapid mixing, the repellent oil blend was dripped onto the corn cobs. The oil did not pool. After about an additional 15 minutes of mixing, spent corn germ was added to the cob-oil composite. Addition of the spent germ was not metered but added in bulk.

The oil-cob-germ composition was then briefly subjected to rapid mixing. Bentonite clay was next added to the mixture and the composite blended for about another 15 minutes. This mixture was conveyed to a feed pelleting line, and the composition then was pelleted using no extraneous steam or heat. A 0.156" (or 5/32") die was used to pellet the composite.

The pelleted material was cooled in an ambient air chamber. Residence time in the chamber was about 5-10 minutes (maximum).

The finished pellets were directly conveyed to a packaging line where the mosquito repellent product was packaged in six pound bottles/jars and capped.

It is thus seen that the invention provides a sustained release pest control composition in some embodiments, and other embodiments, the invention provides methods for controlling a pest. In still further embodiments, the invention provides a method for preparing a pest control agent.

All methods described herein can be performed in any suitable order unless otherwise indicated herein or otherwise clearly contradicted by context. The use of any and all examples and exemplary language provided herein is intended merely to better illuminate the invention and does not pose a limitation on the scope of the invention. No language in the specification should be construed as indicating that any non-claimed element is essential to the practice of the invention.

Preferred embodiments of this invention are described herein, including the best mode known to the inventors for carrying out the invention. Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The references cited herein are incorporated by reference in their entireties, and the specific portions of the references discussed herein are specifically incorporated by reference.

The invention claimed is:

1. A method for repelling pests, comprising applying to a target area an amount of pest control composition effective to repel pests therefrom, the pest control composition comprising discrete plural compacted particles of a carrier and a pest repellent, said carrier comprising a cellulosic fibrous material, said cellulosic fibrous material comprising a corn cob residue, and a mineral sorbent material, said repellent comprising a volatile oil, said carrier further comprising spent corn germ, said mineral sorbent comprising bentonite, said volatile oil being sorbed within said cellulosic fibrous material and said mineral sorbent.

2. A method according to claim 1, said discrete plural particles being in a form of crumbled pelletized material.

3. A method according to claim 2, said discrete plural particles comprising uncoated particles.

4. A method according to claim 1, said repellant comprising a citronella oil and said pest comprising mosquitoes.

5. A method according to claim 1, said repellent further comprising castor oil.

6. A method according to claim 1, said pest control composition being in the form of crumbled pelletized particles.

7. A method according to claim 1, said composition further comprising a binder.

8. A method according to claim 7, said binder comprising a polysaccharide.

* * * * *

UNITED STATES PATENT AND TRADEMARK OFFICE
CERTIFICATE OF CORRECTION

PATENT NO. : 7,846,463 B2  
APPLICATION NO. : 11/382878  
DATED : December 7, 2010  
INVENTOR(S) : Sarjit Johal Page 1 of 1

It is certified that error appears in the above-identified patent and that said Letters Patent is hereby corrected as shown below:

Title Page; item (56);  
Page 1, List of references cited by the Examiner (Other Publications), Column 2, Line 2, delete "Callosobrushus" and insert -- Callosobruchus --

Page 1, List of references cited by the Examiner (Other Publications), Column 2, Line 2, delete "Coleoprera" insert -- Coleoptera --

Page 1, List of references cited by the Examiner (Other Publications), Column 2, Line 3, delete "Techincal" insert -- Technical --

Page 1, List of references cited by the Examiner (Other Publications), Column 2, Line 7, delete "Canadan" insert -- Canadian --

Specification -- Column 1, Lines 4 and 5, delete "BEST CONTROL COMPOSITION AND METHOD"

Claims -- Column 12, Line 21, delete "repellant" and insert -- repellent --

Signed and Sealed this  
Third Day of May, 2011

David J. Kappos  
*Director of the United States Patent and Trademark Office*